June 28, 1949. C. G. DUEHRSEN Plant Pat. 851
POLYANTHA ROSE PLANT
Filed Dec. 17, 1947
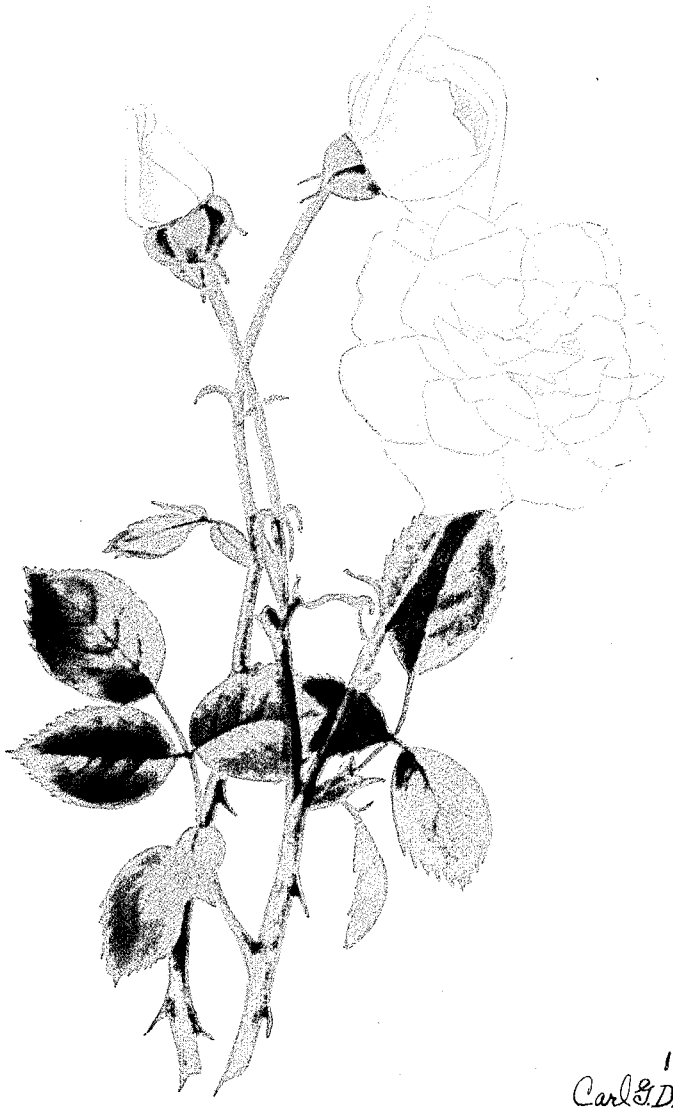
INVENTOR
Carl G. Duehrsen
By Orville M. Kile
Plant Pat. Agt.

Patented June 28, 1949

UNITED STATES PATENT OFFICE

851

POLYANTHA ROSE PLANT

Carl George Duehrsen, Montebello, Calif., assignor to Howard & Smith, Montebello, Calif.

Application December 17, 1947, Serial No. 792,262

1 Claim. (Cl. 47—61)

My present invention relates to a new and distinct variety of polyantha rose plant, with particular reference to its manner of growth. It originated from a cross between Dainty Bess and the hybrid seedling *Rosa gigantea*, with Mme. Cecile Brunner as one of its earlier progenitors.

Although this new variety is more like Mme. C. Brunner than any other variety known to me, it differs greatly, particularly in its manner of growth. Unlike Mme. C. Brunner, its growth is erect.

The flower of my new variety is larger and deeper in color, and the bud is larger and more pointed than Mme. C. Brunner. It is truly a remontant bloomer and is especially adapted to forcing because of its length of stem and excellent keeping qualities.

Accompanying illustrations show in approximately true colors, three typical specimens of the flower of this new variety in various stages of opening, together with portions of the foliage and stems.

In the following detailed description, the usual dictionary meaning of the color nomenclature is intended except that where plate references are given Ridgway's Color Standards and Nomenclature are indicated.

*The plant*

Growth habit: Very erect growth, with long canes.

Blooming habit: Truly remontant. Flowers borne on strong wiry stems.

Disease resistance: No disease apparent in large field cultures in California climate where tested.

Stems:

*Color*—Reddish brown.
*Strength.*—Wiry and strong.
*Rigidity.*—Rigid and erect.
*Thorns.* — Average quantity, prominent, bright red, downward-pointing, scattered, very long for this type of rose.

Foliage: Number of leaflets, 3 to 5.

*Quantity.*—Ample.
*Type.*—Like Mme. Cecile Brunner.
*Shape.*—Broadly oval, with rounded base and acute apex. Serrations very sharp and deep.
*Size.*—Full leaf is 3½ inches long by 2½ inches wide.
*Texture.*—Very leathery.
*Color.*—Dull green.
*Leaf stem.*—Light green with reddish tinge. Stipules broad and long.

Bud:

*Size.*—Approximately 1 inch long.
*Shape.*—Conic. Long-pointed, broad at base.

*Color.*—Deep bright pink.
*Calyx and sepals.*—Short, simple, sharp-pointed, reflex completely in bud stage.
*Peduncle.* — Short, slender but strong. Tinged with reddish brown.

Bloom:

*Borne.*—Average six to a stem.
*Size.*—About 3 inches in diameter.
*Form.*—High centered at first, opening into informal shape with central petals erect and concealing stamens.
*Color.*—Soft pink; a little brighter than Deep Rose Pink (Plate XII).
*Discoloration.*—None.
*Petalage.*—Double, with approximately 30 petals.
*Fragrance.*—Slight.
*Longevity.*—Very excellent keeping qualities.

Petals:

*Shape.*—Obovate, some with slightly ruffled edges.
*Size.*—Average 1½ inches long by 1¼ inches wide.
*Aspects.*—Satiny.
*Texture.*—Leathery.
*Color.*—Uniformly soft pink.
*Persistence.*—Very persistent; cut trusses last a long time.

Reproductive organs:

*Pistils.*—*Styles* light green to dull white. *Stigma* dull red.
*Stamens.*—*Filaments* light red. *Anthers* yellow in bud, changing to dull red. *Pollen* yellow.
*Fruit.*—None.

*Comparison*

The known variey which is most like my new variety is Mme. Cecile Brunner. The chief differences are as follows:

1. My variety grows erect, unlike C. Brunner.
2. My variey has longer canes.
3. My variety has longer and more pointed bud.
4. Flower of my variety is a deeper pink color.
5. Flower of my variey is slightly larger.
6. Flower of my variety has much better keeping qualities.

Having thus disclosed my invention, I claim:

The new and distinct variety of polyantha rose plant of the Mme. C. Brunner type, substantially as herein shown and described, characterized particularly by its erect growth; its long canes; its long pointed bud; and its deep pink flowers of good petalage and excellent keeping qualities.

CARL GEORGE DUEHRSEN.

No references cited.